United States Patent [19]

Young

[11] 4,029,786

[45] June 14, 1977

[54] MORPHOLINE DERIVATIVES FOR TREATING DEPRESSION

[75] Inventor: Edwin Harry Paterson Young, Macclesfield, England

[73] Assignee: Imperial Chemical Industries Limited, London, England

[22] Filed: June 1, 1976

[21] Appl. No.: 691,298

Related U.S. Application Data

[62] Division of Ser. No. 387,378, Aug. 10, 1973, Pat. No. 3,974,158.

[30] Foreign Application Priority Data

Aug. 11, 1972 United Kingdom ............ 37550/72

[52] U.S. Cl. .................... 424/248.56; 424/248.52; 424/248.55
[51] Int. Cl.$^2$ ...................................... A61K 31/535
[58] Field of Search ................. 424/248; 260/247.9

Primary Examiner—Stanley J. Friedman
Attorney, Agent, or Firm—Cushman, Darby & Cushman

[57] ABSTRACT

The disclosure relates to new 2-(substituted anilino)-methylmorpholine derivatives which possess antidepressant activity, to processes for the manufacture of the said morpholine derivatives and to pharmaceutical compositions containing them. Typical of the morpholine derivatives disclosed is 2-(2-ethoxyanilino)methylmorpholine.

4 Claims, No Drawings

MORPHOLINE DERIVATIVES FOR TREATING DEPRESSION

This is a division of application Ser. No. 387,378, filed Aug. 10, 1973, now U.S. Pat. No. 3,974,158.

This invention relates to novel morpholine derivatives which possess valuable antidepressant properties.

According to the invention there is provided a morpholine derivative of the formula:

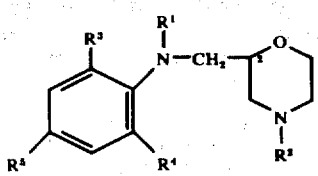

wherein $R^1$ is hydrogen or an aryloxycarbonyl radical of up to 11 carbon atoms; $R^2$ is hydrogen or an alkyl radical of 1 to 6 carbon atoms; and $R^3$, $R^4$ and $R^5$, which may be the same or different, are hydrogen, halogen atoms, or alkyl or alkylthio radicals of 1 to 6 carbon atoms, halogenoalkyl radicals of 1 to 3 carbon atoms, alkoxy radicals of 1 to 10 carbon atoms, alkenyloxy or alkoxycarbonyl radicals of up to 6 carbon atoms, aroyl radicals of up to 11 carbon atoms or aryl or aryloxy radicals of up to 10 carbon atoms; and the pharmaceutically-acceptable acid-addition salts thereof.

It will be observed that the morpholine derivative of the invention possesses an asymmetric carbon atom, marked 2 in the above formula I, and that accordingly such a compound can be isolated in a racemic form and two optically active forms. This specification is addressed to the racemic form of compound I and to both optical isomers; it being a matter of common general knowledge how to resolve the racemic form.

The optically active forms of the compound of formula I possess antidepressant properties to different extents, the compound of the formula I having the (S) absolute configuration about the carbon atom of the morpholine ring bearing the side chain possessing that property to a greater extent than that isomer having the (R) absolute configuration about that carbon atom.

The (R) and (S) system of nomenclature for the absolute configuration of organic compounds is described by R.S. Cahn, C.K. Ingold and V. Prelog in Angew. Chem. Intern. Ed., 1966, 5, 385. The absolute configuration of the compounds of the present invention may be determined by reference to their optical rotatory dispersion (ORD) curves, optical rotatory dispersion being a well known physico-chemical technique described in the standard text-books "Optical Rotatory Dispersion" McGraw-Hill Book Company, Inc., New York, 1960 by C. Djerassi and "Stereochemistry of Carbon Compounds", McGraw-Hill Book Company, Inc., New York, 1962, pages 412–433, by E.L. Eliel. Thus, in the present context, a morpholine derivative having the (S) absolute configuration is one which, as a solution of its hydrochloride salt in methanol, exhibits the same form (positive or negative) of ORD curve as (2S)-2-(2-ethoxyanilino)methylmorpholine hydrochloride whose preparation is described in Example 13.

A particularly suitable value for $R^1$ is hydrogen or a phenoxycarbonyl radical and a particularly suitable value for $R^2$ is hydrogen or a methyl, ethyl, n-propyl or i-propyl radical.

A particularly suitable value for $R^3$, $R^4$ or $R^5$ is a hydrogen, chlorine or fluorine atom, or a methyl, ethyl, n-propyl, i-propyl, methylthio, trifluoromethyl, methoxy, ethoxy, n-propoxy, i-propoxy, n-butoxy, s-butoxy, n-pentyloxy, n-hexyloxy, n-octyloxy, allyloxy, methoxycarbonyl, benzoyl, phenyl, phenoxy or phenylthio radical.

A preferred group of compounds comprises those of formula I wherein $R^1$, $R^2$, $R^4$ and $R^5$ stand for hydrogen.

Particularly preferred compounds are those of the formula I wherein $R^1$, $R^2$, $R^4$ and $R^5$ stand for hydrogen and $R^3$ is an ethoxy, n-propoxy, i-propoxy, s-butoxy or phenoxy radical.

A suitable acid-addition salt of the morpholine derivative of the invention is, for example, a hydrochloride, hydrobromide, phosphate or sulphate or a citrate, acetate, oxalate, methanesulphonate, toluene-p-sulphonate, tartrate, maleate, gluconate or resinate.

The morpholine derivative of the invention may be manufactured by suitable modifications of well known methods, for example:

a. for a compound wherein $R^2$ is hydrogen, and $R^3$, $R^4$ and $R^5$ are other than alkenyloxy radicals, hydrogenolysis of a compound of the formula:

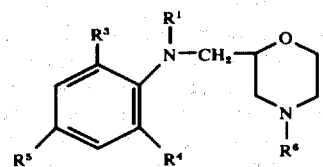

or an acid-addition salt thereof, wherein $R^1$ has the meaning stated above, $R^3$, $R^4$ and $R^5$ have the meanings stated above, apart from alkenyloxy, and $R^6$ is an α-arylalkyl radical of up to 11 carbon atoms.

The α-arylalkyl radical is preferably a benzyl radical and the hydrogenolysis is preferably carried out by means of hydrogen in the presence of a palladium on charcoal catalyst, in a diluent or solvent; the catalytic hydrogenolysis is conveniently carried out at ambient temperature and atmospheric pressure and is conveniently accelerated by the presence of an acidic catalyst, for example hydrochloric acid;

b. for a compound wherein $R^1$ is hydrogen, hydrolysis of a compound of the formula:

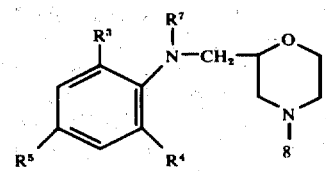

wherein $R^3$, $R^4$ and $R^5$ have the meanings stated above and $R^7$ is hydrogen or an acyl radical of up to 11 carbon atoms and $R^8$ is hydrogen, an alkyl radical of 1 to 6 carbon atoms or an acyl radical of up to 11 carbon atoms, provided that when $R^7$ is hydrogen, then $R^8$ is an acyl radical of up to 11 carbon atoms. The acyl radical of up to 11 carbon atoms may be an aryloxycarbonyl radical, for example a phenoxycarbonyl radical, or it may be an alkanoyl radical, for example an acetyl radical. The hydrolysis may be carried out with an acid, for example hydrochloric or sulphuric acid, or a base, for example sodium hydroxide or potassium hydroxide, in a diluent or solvent, for example water, an alcohol or aqueous alcohol, for example methanol or ethanol, or dimethylsulphoxide. The hydrolysis may be accelerated or completed by the application of heat, for example at 100° C. or at the boiling point of the solvent.

c. the reaction of a compound of the formula:

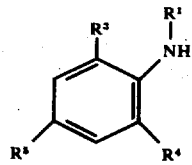

with a compound of the formula:

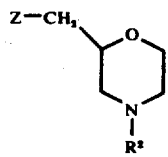

wherein $R^1$, $R^2$, $R^3$, $R^4$ and $R^5$ have the meanings stated above and wherein Z stands for a halogen atom, for example a chlorine or bromine atom, or for an alkane- or arene- sulphonyloxy radical, for example a methanesulphonyloxy or toluene-p-sulphonyloxy radical. The process may be carried out using the salt of a compound of the formula IV, made by reaction of the compound with a strong base, for example an alkali metal or an amide or hydride thereof, for example sodium hydride. The process may be carried out in a diluent or solvent, for example dimethylformamide, dimethylsulphoxide, dioxan or dimethoxyethane and it may be carried out at an elevated temperature, for example a temperature of up to 150° C.

d. for a compound in which $R^1$ is hydrogen, heating a compound of the formula:

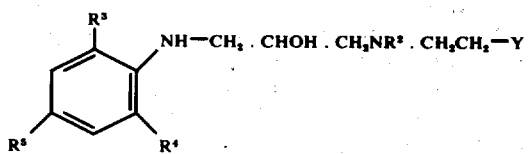

or an acid-addition salt thereof, wherein $R^2$, $R^3$, $R^4$ and $R^5$ have the meanings stated above and wherein Y stands for a halogen atom, for example a chlorine or bromine atom, or for a sulphonyloxy radical, for example a radical of the formula $OSO_2OR^9$ wherein $R^9$ stands for hydrogen or for a lower alkyl or an aryl radical, for example the methyl, ethyl, phenyl or p-tolyl radical, with a base.

The process may be carried out in a diluent or solvent, for example water, an alcohol, for example methanol, ethanol, isopropanol, n-butanol, t-butanol or ethylene glycol, or an ether, for example diethyl ether, dimethoxyethane, tetrahydrofuran or dioxan, or a mixture of any of the abovementioned solvents; it may be carried out at ambient temperature or at a temperature up to the boiling point of the diluent or solvent, for example at a temperature of between 40° and 100° C., and it may be carried out in the presence of an alkali or alkaline earth metal hydroxide, for example sodium, potassium or barium hydride.

e. for a compound which is an (R) or an (S) isomer, either resolution of a compound of formula I by conventional means, for example separation by fractional crystallisation of the mixture of diastereoisomeric acid-addition salt with an optically active acid, or employment of any one of processes (a) to (d) using an optically active intermediate which has itself been resolved by conventional means.

The starting material of the formula II for process (a) may be obtained by the reaction of a compound of the formula IV with a compound of the formula:

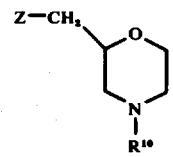

wherein $R^{10}$ is an α-arylalkyl radical.

The starting material of the formula III for use in process (b) may be prepared, for example, by reaction of 2-toluene-p-sulphonyloxymethylmorpholine, or its corresponding 4-acyl or 4-protected derivative, with a substituted aniline or N-acylaniline, followed by removal of the protecting group if necessary.

The starting material of the formula V in which $R^2$ is an alkyl radical of 1 to 6 carbon atoms may be prepared, for example, by reaction of allylglycidyl ether with an alkylamine followed by acylation of the product with chloroacetyl chloride and subsequent ring closure to give the 2-allyloxymethyl-4-alkylmorpholin-5-one. This lactam is reduced with $LiAlH_4$, the allyl group is cleaved and the resulting alcohol reacted with toluene-p-sulphonyl chloride.

The starting material of the formula VI for use in process (d) may be prepared by reaction of an amine of the formula:

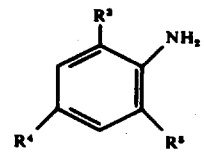

with epichlorhydrin, followed by reaction of the product with a compound of the formula $HNR^2.CH_2CH_2Y$.

The compounds of the invention possess antidepressant activity in warm-blooded animals as demonstrated by the reversal of reserpine-induced hypothermia in mice. All clinically useful antidepressants have a calorigenic action in reserpinised mice, and this test is the one primarily used in the art for establishing relative anti-depressant activity in a series of related compounds. (Askew, *Life Sciences*, 1963, volume 2, page 725).

The test, known as the RHL test, is carried out as follows:

Each member of various groups of 6 mice was given reserpine (2 mg. of base per kg. bodyweight, given subcutaneously, as the phosphate). Seventeen hours later, the gastric temperature (To) of each mouse was recorded by means of an orally-inserted probe coupled to an electric thermometer which was calibrated in degrees Centigrade and which could be read to 0.05° C. Immediately after the temperature measurement, the mice were dosed orally with the test compound or with saline (controls), each mouse in a group of 6 being given the same substance, and the gastric temperatures were again recorded after 4 hours ($T_4$). The effect of the test compound was computed from the mean cumulative rise in temperature after 4 hours. The mean cumulative difference in temperature (C) is thus defined as the mean, calculated from the results obtained in 6 mice, of the sum:

$$T_4 - T_o$$

The effect of the test compound is related to the dose, and, using suitable doses, a dose of compound can be defined which gives a mean cumulative rise in temperature of 3° C. greater than that of control mice. This dose is called the $ED_3$ and is recorded in mg. per kg. bodyweight.

All the compounds exemplified in this specification are active on the RHL test at a dose ($ED_3$) of equal to or less than 30 mg./kg. while at the same dose showing no obvious signs of toxicity. A number of compounds, including 2-(2-ethoxyanilino)methylmorpholine, 2-(2-n-propoxyanilino)methylmorpholine, 2-(2-n-butoxyanilino)methylmorpholine, 2-(2-ethylanilino)methylmorpholine and 2-(2-phenoxyanilino)methylmorpholine showed no obvious toxicity at oral doses of up to 400 mg/kg. in mice.

According to a further feature of the invention, there is provided a pharmaceutical composition which comprises as active ingredient a morpholine derivative of the invention, in association with a non-toxic, pharmaceutically-acceptable diluent or carrier therefor.

The pharmaceutical composition may be, for example, in a form suitable for oral or parenteral administration, for which purposes it may be formulated by means known to the art into the form of, for example, tablets, capsules, aqueous or oily solutions or suspensions, emulsions, sterile injectable aqueous or oily solutions or suspensions, or dispersible powders.

The pharmaceutical composition of the invention may also contain, in addition to the morpholine derivative or salt thereof, one or more known drugs selected from neuroleptic-sedative agents, for example chlorpromazine, prochlorperazine, trifluoperazine and haloperidol; other sedative drugs and tranquillizers, for example chlordiazepoxide, phenobarbitone and amylobarbitone; $\beta$-adrenergic blocking agents, for example propranolol; drugs used in the treatment of Parkinson's disease, for example benzhexol; and other antidepressant drugs, for example imipramine, desipramine, amitriptyline, nortriptyline, drugs of the amphetamine type and monoamineoxidase inhibitors, for example phenelzine and mebanazine.

A preferred pharmaceutical composition of the invention is one suitable for oral administration in unit dosage form, for example tablets and capsules, which contain between 20 and 200 mg. of active ingredient, or one suitable for intravenous or intramuscular injection, for example a sterile aqueous solution containing between 0.5 and 4% w/w of active ingredient.

The pharmaceutical composition of the invention will normally be administered to man for the treatment or prophylaxis of depressive illness, at such a dose that each patient receives a total oral dose of between 150 and 400 mg. of active ingredient per day, or a total intravenous or intramuscular dose of between 40 and 80 mg. per day, the composition being administered 2 to 3 times per day.

The invention is illustrated, but not limited, by the following Examples:

EXAMPLE 1

A solution of 4-benzyl-2-(2-ethoxyanilino)-methylmorpholine dihydrochloride (2.0 g.) in methanol (50 ml.) is shaken in an atmosphere of hydrogen in the presence of 5% palladium/carbon catalyst until a molar equivalent of hydrogen has been absorbed. The solution is filtered, the methanol evaporated and the residue dissolved in water and the solution thus obtained is basified with dilute sodium hydroxide solution. The mixture is extracted with ether (3 × 100 ml.) and the ethereal solution is dried ($MgSO_4$), filtered and treated with an ethereal solution of oxalic acid. The precipitated oxalate is recrystallised from acetone to give 2-(2-ethoxyanilinomethyl)morpholine oxalate, m.p. 157° C. The corresponding hydrochloride has m.p. 180°–182° C. on recrystallisation from ethanol, and the maleate has m.p. 143°–145° C. on recrystallisation from methanol/ethyl acetate.

The 4-benzyl-2-(2-ethoxyanilino)methylmorpholine dihydrochloride used as starting material may be prepared as follows:

A mixture of 2-ethoxyaniline (14.0 g.) and 4-benzyl-2-toluene-p-sulphonyloxymethylmorpholine (18.6 g.) is stirred and heated on the steam bath (95° C.) under nitrogen for 24 hours. The mixture is cooled and ether added. The solid thus obtained is collected and crystallised from ethyl acetate to give 4-benzyl-2-(2-ethoxyanilino)methylmorpholine toluene-p-sulphonate, m.p. 127° C. The toluene sulphonate salt is converted into the corresponding dihydrochloride by basifying it with dilute sodium hydroxide solution, extracting the base into ether (3 × 200 ml.), washing the ethereal extract with water and then drying it over anhydrous magnesium sulphate followed by filtration and treatment of the ethereal solution of base with ethereal hydrochloric acid solution. The 4-benzyl-2-(2-ethoxyanilino)-methylmorpholine dihydrochloride melts at 226° C. after crystallisation from methanol/ethyl acetate.

The 4-benzyl-2-toluene-p-sulphonyloxymethylmorpholine used as starting material may be obtained as follows:

To a solution of 4-benzyl-2-hydroxymethylmorpholine (118.8 g.) in dry pyridine (250 ml.) toluene-p-sulphonyl chloride (120.2 g.) is added gradually at 18°–25° C. The mixture is stirred for 20 hours at ambient temperature (ca. 20° C.) and the pyridine is removed under diminished pressure. The residue is diluted with water, the mixture made alkaline by the addition of sodium hydroxide solution, and the product is then extracted into ether. The ethereal solution is dried ($MgSO_4$) and filtered, the ether is evaporated and the residual solid is crystallised from cyclohexane or petroleum ether (b.p. 60°–80° C.) to give 4-benzyl-2-toluene-p-sulphonyloxymethylmorpholine, m.p. 78°–79° C.

EXAMPLE 2

The process described in the first part of Example 1 is repeated except that the appropriate N-benzyl anilinomethylmorpholine dihydrochloride is used as starting material in place of 4-benzyl-2-(2-ethoxyanilino)methylmorpholine dihydrochloride. The following compounds are thus obtained:

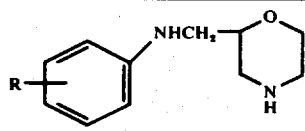

| R | Reaction Solvent | Salt | m.p. (° C.) | Recrystallisation Solvent |
|---|---|---|---|---|
| 4-ETO | methanol | oxalate | 156–157 | methanol/ether |
| 4-F | methanol | dioxalate | 117–119 | methanol/ether |
| 2,4-diMeO | water | dioxalate | 160–161 | methanol/ether |
| 4-MeO | water | dioxalate | 205 (decomp.) | methanol/ether |

The starting materials used in the above process may be obtained by repeating the process described in the second part of Example 1 using an equivalent amount of the appropriate substituted aniline as starting material in place of 2-ethoxyaniline. The following compounds are thus obtained:

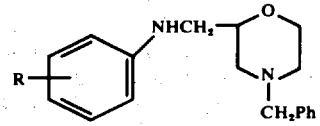

| R | Salt | m.p. (° C.) | Recrystallisation Solvent |
|---|---|---|---|
| 4-EtO | dihydrochloride | 220–222 | methanol/ethyl acetate |
| 4-F | dihydrochloride | 233–236 | methanol/ethyl acetate |
| 2,4-diMeO | dihydrochloride monohydrate | 216–219 | methanol/ethyl acetate |
| 4-MeO | dihydrochloride monohydrate | 232–233 | methanol/ethyl acetate |

EXAMPLE 3

The process described in the first part of Example 1 is repeated except that the appropriate 4-benzyl anilinomethylmorpholine salt is used as starting material in place of 4-benzyl-2-(2-ethoxyanilino)methylmorpholine dihydrochloride. The following compounds are thus obtained

| R | Salt Used | Reaction Solvent | Salt Prepared | m.p. (° C.) | Recrystallisation Solvent |
|---|---|---|---|---|---|
| 2-n-PrO | toluene-p-sulphonate | ethanol | hydrochloride | 125–127 | ethanol/ether |
| 2-i-PrO | toluene-p-sulphonate | ethanol | toluene-p-sulphonate | 70–71 | water |
| 2-MeO | toluene-p-sulphonate | ethanol/water | toluene-p-sulphonate | 138–140 | ethanol/ether |
| 2-n-BuO | dihydrochloride | ethanol | oxalate | 108–112 | ethanol/ether |
| 2PhO | dihydrochloride | ethanol | dihydrochloride | 184–188 | ethanol/acetone |
| 2-n-C$_6$H$_{13}$O | toluene-p-sulphonate | ethanol | oxalate | 78–82 | ethyl acetate |
| 2-n-C$_5$H$_{11}$O | toluene-p-sulphonate | ethanol | toluene-p-sulphonate | 117–119 | water |
| 2-Ph | toluene-p-sulphonate | ethanol | toluene-p-sulphonate | 146–147 | ethyl acetate/ethanol |
| 2-n-C$_8$H$_{17}$O | toluene-p-sulphonate | ethanol | toluene-p-sulphonate | 80–83 | ethyl acetate/60–80 petrol. |
| 2-S-BuO | toluene-p-sulphonate | ethanol | hemitartrate | 112–114 | acetone |
| 2,6-di-i-Pr | toluene-p-sulphonate | water/ethanol | oxalate | 167–169 (decomp.) | ethyl acetate ethanol |
| 2CH$_3$OOC | toluene-p-sulphonate | water/methanol | toluene-p-sulphonate | 137–140 | methanol/ether |
| 2,6-di-Me | dihydrochloride | water | dioxalate | 117–123 | methanol/ether |
| 2,4-di-EtO | dihydrochloride | ethanol | oxalate | 151–153 | methanol |
| 2-Et | dihydrochloride | ethanol | oxalate | 142–144 | methanol/ether |
| 2,4,6-tri-Me | dihydrochloride | ethanol | oxalate | 141–143 | ethanol/ether |
| 2-CF$_3$ | toluene-p-sulphonate | ethanol | toluene-p-sulphonate | 150–153 | methanol/ether |

The starting materials used in the above process may be obtained by repeating the process described in the second part of Example 1 using an equivalent amount of the appropriate substituted aniline in place of 2-ethoxyaniline. For some of the compounds, the reaction is conducted in refluxing xylene for 2 days. The following compounds are thus obtained:

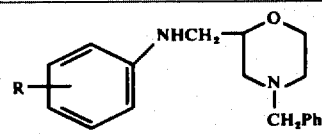

| R | Salt | m.p. | Recrystallisation Solvent | Xylene as Solvent |
|---|---|---|---|---|
| 2-n-PrO | toluene-p-sulphonate | 132–134 | ethyl acetate | No |
| 2-i-PrO | toluene-p-sulphonate | 129–131 | ethyl acetate | No |
| 2-MeO | toluene-p-sulphonate | 161–162 | acetone | No |
| 2-n-BuO | dihydrochloride | 151–154 | ethanol/ether | No |
| 2-PhO | dihydrochloride | 168–174 | acetone | Yes |
| 2-n-C$_4$H$_{13}$O | toluene-p-sulphonate | 106–109 | ethyl acetate/ether | Yes |
| 2-n-C$_5$H$_{11}$O | toluene-p-sulphonate | 130–132 | ethyl acetate | Yes |
| 2-Ph | toluene-p-sulphonate | 132–138 | xylene | Yes |
| 2-n-C$_8$H$_{17}$O | toluene-p-sulphonate | 110–112 | ethyl acetate/petrol. (60–80) | Yes |
| 2-s-BuO | toluene-p-sulphonate | 158–160 | ethyl acetate | Yes |
| 2,6-di-i-Pr | toluene-p-sulphonate | 134–138 | ethyl acetate | Yes |
| 2-CH$_3$OOC | toluene-p-sulphonate | 175–177 | methanol/ether | Yes |
| 2,6-di-Me | dihydrochloride | 200 (decomp.) | methanol/ether | No |
| 2,4-di-EtO | dihydrochloride | 190–198 (decomp.) | methanol/ether | No |
| 2-Et | dihydrochloride | 146–149 | methanol/ether | No |
| 2,4,6-tri-Me | dihydrochloride | 224–227 | methanol/ether | No |
| 2-CF$_3$ | hydrochloride | 172–175 | methanol/ether | No |

EXAMPLE 4

A solution of 4-benzyl-2-(N-phenoxycarbonylanilino)methylmorpholine hydrochloride (9 g.) in water (75 ml.) and ethanol (200 ml.) is shaken in an atmosphere of hydrogen in the presence of palladium on charcoal catalyst (0.5 g.; 5%) until no further hydrogen is absorbed. The catalyst is removed by filtration and the filtrate is then evaporated to give a white residue which is recrystallised from methanol/ether to give 2-(N-phenoxycarbonylanilino)methylmorpholine hydrochloride, m.p. 179°–181° C.

The 4-benzyl-2-(N-phenoxycarbonylanilino)methylmorpholine hydrochloride used as starting material may be obtained as follows:

To a solution of 4-benzyl-2-anilinomethylmorpholine (8.1 g.) in toluene (50 ml.) and hexamethylene phosphoramide (2 ml.) is added phenylchloroformate (8 ml.). A white precipitate forms which does not dissolve when the mixture is refluxed for 4 hours. The solid (10.15 g.) is crystallised from ethanol to given 4-benzyl-2-(N-phenoxycarbonylanilino)-methylmorpholine hydrochloride, m.p. 248°–250° C.

EXAMPLE 5

Phenyl chloroformate (3.1 g.) is added to a solution of 4-benzyl-2-(2-allyloxyanilino)methylmorpholine (3 g.) in toluene (70 ml.) and the mixture is heated under reflux for 4 hours. The toluene is distilled off under reduced pressure and the residual oil of 2-(2-allyloxy-N-phenoxycarbonylanilino)methyl-4-phenoxycarbonylmorpholine is then heated under reflux for 18 hours with potassium hydroxide (6 g.), water (10 ml.) and ethanol (40 ml.). The mixture is poured into water (400 ml.) and extracted with ether (3 × 200 ml.). The ethereal extract is dried (MgSO$_4$), filtered and the filtrate is treated with an ethereal solution of oxalic acid. The crude product is recrystallised from ethanol/ether to give 2-(2-alloyloxyanilino)methylmorpholine oxalate, m.p. 146°–150° C. (decomposition).

The above process is repeated using an equivalent amount of the appropriate 4-benzylanilinomethylmorpholine in place of 4-benzyl-2-(2-allyloxyanilino)methylmorpholine. The hydrolysis of the phenoxycarbonyl derivative may be effected by heating with sodium hydroxide in dimethylsulphoxide (NaOH/DMSO- prepared by adding a calculated quantity of water to a solution of sodium methylsulphinylmethide in dimethylsulphoxide) or with 50% sulphuric acid. The following compounds are thus prepared:

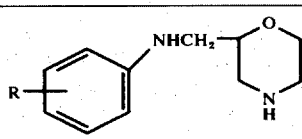

| R | Reaction Solvent | Hydrolysis Conditions | Salt | M.P. (° C.) | Crystallisation Solvent |
|---|---|---|---|---|---|
| 2-MeS | toluene | KOH/water/ethanol | oxalate | 164–166 | methanol/ether |
| H | * | 50% H$_2$SO$_4$ | hydrate oxalate | 102–106 | methanol/ether |
| 2-PhS | toluene | NaOH/DMSO | oxalate | 175–178 | methanol/ether |

-continued

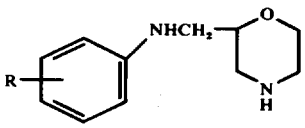

| R | Reaction Solvent | Hydrolysis Conditions | Salt | M.P. (° C.) | Crystallisation Solvent |
|---|---|---|---|---|---|
| 2-PhCO | ** | NaOH/DMSO | hydrogen oxalate | 182–184 | methanol/ether |

The 4-benzyl-2-(2-allyloxyanilino)methylmorpholine used as starting material in the above process may be obtained as follows:

A solution of 2-allyloxyaniline (1.5 g.) and 4-benzyl-2-toluene-p-sulphonyloxymethylmorpholine (3 g.) in ethanol (20 ml.) is heated under reflux for 4 days and the ethanol is then evaporated. The residual gum is first triturated with ether and then dissolved in water and the free base liberated by treatment with sodium hydroxide solution. The base is extracted into ether and the extract is washed with water, dried over anhydrous magnesium sulphate, filtered and then treated with an ethereal solution of oxalic acid to given 4-benzyl-2-(2-allyloxyanilino)methylmorpholine oxalate, m.p. 166°–170° C. (decomposition) on recrystallisation from ethanol from which the free base is obtained by standard procedure.

The 4-benzyl-2-(2-methylthioanilino)methylmorpholine and 4-benzyl-2-(2-phenylthioanilino)methylmorpholine used as starting materials may be obtained by repreating the process described in the second part of Example 1 using 2-methylthioaniline and 2-phenylthioaniline in place of 2-ethoxyaniline. There are thus obtained 4-benzyl-2-(2-methylthioanilino)methylmorpholine dihydrochloride, m.p. 194°–197° C. on recrystallisation from methanol/ether and 4-benzyl-2-(2-phenylthioanilino)methylmorpholine toluene-p-sulphonate respectively, from which the free bases are obtained by standard procedures.

The starting material for this reaction may be prepared as follows:

To a solution of 4-benzyl-2-toluene-p-sulphonyloxymethylmorpholine (5 g.) in dichloromethane (50 ml.), phenylchloroformate (2 ml.) is added and the mixture is stirred at ambient temperature (ca 20° C.) for 24 hours. The solvent is evaporated and the residual oil is recrystallised from ethanol to given 4-phenoxycarbonyl-2-toluene-p-sulphonyloxymethylmorpholine, m.p. 101°–103° C.

The 2-(2-benzoylanilinomethyl)-4-phenoxycarbonylmorpholine used as starting material may be prepared as follows:

A solution of 2-aminobenzophenone (1.97 g.) in dry dimethylformamide (30 ml.) is treated at ambient temperature with an 80% mineral oil dispersion of sodium hydride (0.3 g.). The mixture is stirred until effervescence ceases and a clear solution is obtained. There is then added 4-phenoxycarbonyl-p-toluene-p-sulphonyloxymethylmorpholine (3.8 g.) and the mixture is stirred and heated at 120° C. for 18 hours. The mixture is diluted with water (100 ml.) and extracted with ethyl acetate (3 × 50 ml.). The combined ethyl acetate extracts are washed with water (5 × 50 ml.), dried over anhydrous magnesium sulphate and the solvent is removed under reduced pressure. There is thus obtained 2-(2-benzoylanilino)methyl-4-phenoxycarbonylmorpholine as a gum which is not further purified.

EXAMPLE 6

The hydrolysis process described in the first part of Example 4 is repeated, using 2-(N-phenoxycarbonylanilino)methylmorpholine as starting material in place of 2-(2-allyloxyanilino)methyl-4-phenoxycarbonylmorpholine, and carrying out the hydrolysis with NaOH/DMSO. There is thus obtained 2-anilinomethylmorpholine oxalate, m.p. 103°–107° C. on recrystallisation from methanol/ether.

The 2-(N-phenoxycarbonylanilino)methylmorpholine used as starting material may be obtained as follows:

The process described in the first part of Example 1 is repeated using 4-benzyl-2-(N-phenoxycarbonylanilino)methylmorpholine hydrochloride as starting material in place of 4-benzyl-2-(2-ethoxyanilino)methylmorpholine dihydrochloride. There is thus obtained 2-(N-phenoxycarbonylanilino)methylmorpholine hydrochloride, m.p. 170°–181° C. on recrystallisation from methanol/ether, from which the free base is obtained by standard procedure.

EXAMPLE 7

A solution of 2-ethoxyaniline (4.8 g.) and 4-n-propyl-2-toluene-p-sulphonyloxymethylmorpholine (10 g.) in xylene (50 ml.) is heated under reflux in an atmosphere of nitrogen for 60 hours. As resinous solid separates from the solvent which is distilled under reduced pressure. The residual sticky solid is washed with ether to give a yellow solid which is crystallised from methanol/ether to give 2-(2-ethoxyanilino)methyl-4-propylmorpholine toulene-p-sulphonate, m.p. 169°–172° C.

The 4-n-propyl-2-toluene-p-sulphonyloxymethylmorpholine used as starting material may be prepared as follows:

Allylglycidyl ether (94.7 g.) is added with stirring to a solution of n-propylamine (98 g., 137 ml.) in ethanol (200 ml.). The mixture is heated under reflux for 18 hours and the solvent in excess of n-propylamine are distilled off. The residual oil is distilled and the fraction b.p. 79°–85° C. at 1 m.m. is collected to give 1-allyloxy-3-n-propylamino-2-propanol.

A solution of 1-allyloxy-3-n-propylamino-2-propanol (95.2 g.) in a mixture of dry methylene chloride (275 ml.), and triethylamine (80 ml.) is cooled to between −5° and 0° C. and a solution of chloroacetylchloride (42 ml.) in methylene chloride (60 ml.) is added dropwise with stirring during 2 hours. The mixture is allowed to warm to ambient temperature (18°–20° C.) and stirred at this temperature for 18 hours. The solution is washed with 2N hydrochloric acid (2 × 100 ml.) and then with water (100 ml.) and dried (MgSO₄). Removal of the solvent under reduced pressure gives N-(3-allyloxy-2-hydroxypropyl)-N-n-propyl-α-chloroacetamide (119.7 g.) as an oil which is used without further purification.

A solution of N-(3-allyloxy-2-hydroxypropyl)-N-n-propyl-α-chloroacetamide (119.7 g.) in methanol is added to a solution of sodium methoxide prepared by dissolving sodium (13 g.) in methanol (900 ml.). The mixture is stirred and heated under reflux for 18 hours and the solvent is then distilled off. Water (400 ml.) is added to the residue and the resulting mixture is extracted with ethyl acetate (1 × 400 ml.; 2 × 200 ml.). The combined extracts are washed with water, dried (MgSO₄), filtered and the filtrate is evaporated. The residual oil is distilled and the fraction b.p. 123°–125° C. at 0.7 m.m. is collected. There is thus obtained 2-allyloxymethyl-4-n-propylmorpholin-5-one (65.2 g.).

A solution of 2-allyloxymethyl-4-n-propylmorpholin-5-one (65 g.) in dry ether (100 ml.) is added slowly with stirring to a suspension of lithium aluminium hydride (17.5 g.) in dry ether (700 ml.). The rate of addition is adjusted so that the reaction mixture refluxes gently. When the addition is complete the reaction mixture is stirred at ambient temperature (18°–20° C.) for 18 hours and then water (90 ml.) is added very carefully dropwise to decompose the complex and excess of lithium aluminium hydride. The ethereal solution is filtered and the solid residue is washed with ether. The filtrate and ethereal washings are combined, dried (Na₂SO₄), filtered and the ether evaporated. The product, 2-allyloxymethyl-4-n-propylmorpholine is obtained as an oil b.p. 80°–90° C. at 1 m.m. which forms a hydrogen oxalate, m.p. 125°–127° C.

2-Allyloxymethyl-4-n-propylmorpholine (59.7 g.) is heated under reflux in hydrochloric acid (240 ml.; 20%) for 18 hours. The solution is cooled, diluted with ice and water, basified with sodium hydroxide and extracted with ether (3 × 200 ml..). The ethereal solution is dried (MgSO₄), filtered and the ether evaporated to give recovered starting material. The aqueous layer is concentrated to a small volume and precipitated salt is removed by filtration and washed with ether. The filtrate is extracted with ether (3 × 100 ml.) and the combined extracts and ethereal wash are dried (MgSO₄), filtered and the ether evaporated. 2-Hydroxymethyl-4-n-propylmorpholine (16.7 g.) is obtained as a viscous oil which forms a hydrogen oxalate, m.p. 133°–135° C. after crystallisation from a methanol/ether mixture.

2-Hydroxymethyl-4-n-propylmorpholine (16.2 g.) is dissolved in dry pyridine (50 ml.) and a solution of toluene-p-sulphonylchloride (21.4 g.) in dry pyridine (50 ml.) is added dropwise with stirring. The mixture is stirred at 20°–25° C. for 3 hours. The pyridine is removed under reduced pressure, water (100 ml.) is added to the residue and the product is extracted into ether (3 × 150 ml.). The ethereal solution is washed with water, dried (MgSO₄), filtered and the ether evaporated to give 4-n-propyl-2-toluene-p-sulphonyloxymethylmorpholine (30.6 g.) as an oil which forms a hydrochloride, m.p. 172°–173° C. on recrystallisation from methanol/ether.

Example 8

A solution of 2-toluene-p-sulphonyloxymethylmorpholine (prepared by standard procedure from its acetate salt) (1.5 g.) in dimethylsulphoxide (12 ml.) is added to a solution of the sodium salt of o-phenetidine [prepared from a solution of o-phenetidine (1 g.) in dimethylsulphoxide by adding sodium hydride (0.3 g.: 60% dispersion) under nitrogen and stirring for 1 hour] and the mixture is heated at 100° C. in an atmosphere of nitrogen for 48 hours, then cooled, diluted with water and extracted with ether (3 × 100 ml.). The ethereal extract is washed with water (2 × 50 ml.), dried and the ether evaporated to give an oil. The oil is dissolved in methanol (2 ml.) and placed on a column of magnesium silicate which is then eluted with methanol. The eluate is collected and the methanol is evaporated to give a residue which is dissolved in ether. Ethereal hydrogen chloride is then carefully added to give a monohydrochloride which is recrystallised from an ethanol/ether mixture to give 2-(2-ethoxyanilino)methylmorpholine hydrochloride, m.p. 179°–182° C. The 2-toluene-p-sulphonyloxymethylmorpholine acetate used as starting material may be prepared as follows:

A solution of 4-benzyl-2-toluene-p-sulphonyloxymethylmorpholine (18.75 g.) in glacial acetic acid (50 ml.) is shaken in an atmosphere of hydrogen with palladium on carbon catalyst (0.5 g.; 5%) until no more hydrogen is absorbed (ca. 1.1 l.). The catalyst is then removed by filtration and the filtrate is evaporated under reduced pressure to give a colourless syrup which, on addition of ethanol, solidifies. Crystallisation from ethanol gives 2-toluene-p-sulphonyloxymethylmorpholine acetate, m.p. 140°–142° C.

EXAMPLE 9

A mixture of 2-(N-acetyl-2-ethoxyanilino)methylmorpholine hydrochloride (2 g.) and concentrated hydrochloric acid is heated under reflux for 24 hours. The solution is cooled, diluted with ice (25 g.), basified with sodium hydroxide solution and extracted with ether (2 × 100 ml.). The ether extract is dried (Na₂SO₄) and treated with ethereal HCl to give 2-(2-ethoxyanilino)methylmorpholine hydrochloride, m.p. 180°–181° C.. on recrystallisation from ethanol.

The 2-(N-acetyl-2-ethoxyanilino)methylmorpholine hydrochloride used as starting material may be prepared as follows:

A solution of 4-benzyl-2-(2-ethoxyanilino)methylmorpholine (14.0 g.) (obtained from the dihydrochloride salt whose preparation is described in Example 1) in acetic anhydride is heated at 95°–100° C. for 3 hours. The reaction mixture is cooled, poured into ice and water (500 g.) then basified with sodium hydroxide and extracted with ether (2 × 250 ml.). The ether solution is dried (MgSO₄) and treated with ethereal HCl to give 4-benzyl-2-(N-acetyl-2-ethoxyanilino)methylmorpholine hydrochloride, m.p. 174°–176° C. on recrystallisation from acetone/ethyl acetate.

The process described in the first part of Example 1 is then repeated except that 4-benzyl-2-(N-acetyl-2-ethoxyanilino)methylmorpholine hydrochloride is used as starting material in place of 4-benzyl-2-(2-ethoxyanilino)methylmorpholine dihydrochloride. There is thus obtained 2-(N-acetyl-2-ethoxyanilino)methylmorpholine hydrochloride, m.p. 159°–162° C. after recrystallisation from acetone/ether.

EXAMPLE 10

The process described in the first part of Example 9 is repeated using the appropriate 2-(N-acetylanilino)-methylmorpholine in place of 2-(N-acetyl-2-ethoxyanilino)methylmorpholine hydrochloride. The hydrolysing acid may be 50% sulphuric acid and the duration of the reaction may be varied. The following compounds are thus obtained:

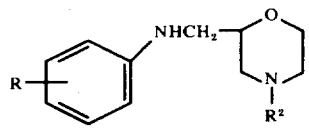

| R¹ | R² | Salt Used | Acid Used | Duration of heating (hrs.) | Product | m.p. °C. | Crystallisation Solvent |
|---|---|---|---|---|---|---|---|
| H | H | oxalate | conc. HCl | 18 | oxalate | 102–106 | methanol/ether |
| 2-Cl | H | hydrogen oxalate | conc. HCl | 18 | oxalate | 172–173 | methanol/ether |
| 2-Me | H | hydrogen oxalate | conc. HCl | 72 | oxalate | 159–162 | methanol/ether |
| 4-Me-2-n-Pr | H | hydrogen oxalate | 50% $H_2SO_4$ | 18 | oxalate hemi-hydrate | 86–88 | ethanol/ether |
| 2-PhCH$_2$ | H | base | conc. HCl | 18 | oxalate | 164–167 decomp.) | methanol |
| 2-EtO | Me | hydrogen oxalate | conc. HCl | 48 | di-hydrogen oxalate | 130–132 | acetonitrile |
| 2-EtO | n-Pr | hydrogen oxalate | conc. HCl | 48 | toluene-p-sulphonate | 169–172 | methanol/ether |

Some of the 2-(N-acetylanilinomethyl)morpholines used as starting materials may be prepared by repeating the process described in the first part of Example 1, using the appropriate 2-(N-acetylanilino)methyl-4-benzylmorpholine in place of 4-benzyl-2-(2-ethoxyanilino)methylmorpholine dihydrochloride as starting material. The following compounds are thus obtained:

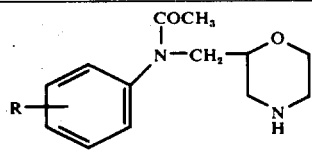

| R | Salt Used | Reaction Solvent | Product | m.p. (°C.) | Re-crystallisation Solvent |
|---|---|---|---|---|---|
| H | hydrogen oxalate | ethanol | hydrogen oxalate | 176–178 | methanol/ether |
| 2-Cl | hydrogen oxalate | ethanol | hydrogen oxalate |  | not purified |
| 2-Mc | hydrogen oxalate | ethanol | hydrogen oxalate | 154–157 | methanol/ether |
| 2-n-Pr-4-Me | oxalate | water/ethanol | hydrogen oxalate | 181–183 | methanol/ether |

The 2-(N-acetyl-2-benzylanilino)methylmorpholine used as starting material may be prepared as follows:

To a stirred suspension of sodium hydride (80% dispersion in oil; 0.6 g.) in dry dimethylformamide (80 ml.) is added 2-benzylacetanilide (2.25 g.) under nitrogen. When the effervescence has ceased 2-toluene-p-sulphonyloxymethylmorpholine acetate (3.3 g.) is added, the reaction mixture is stirred for 2 hours and then poured into water. The resulting mixture is extracted with ethyl acetate, this extract extracted with aqueous hydrochloric acid, the acidic extract neutralised and extracted with ethyl acetate. The ethyl acetate is washed with water, dried (MgSO$_4$) and distilled to give 2-(N-acetyl-2-benzylanilino)methylmorpholine as a thick oil which is used without further purification.

The 2-(N-acetyl-2-ethoxyanilino)-4-methylmorpholine used as starting material may be prepared as follows:

A mixture of 2-(N-acetyl-2-ethoxyanilino)methylmorpholine hydrochloride (10 g.), formic acid (25 ml.) and formaldehyde (25 ml.; 40% solution) is heated at 95°–100° C. for 8 hours, poured onto ice (ca. 500 g.), basified (pH 11) with sodium hydroxide solution (40%) and extracted with ether (2 × 200 ml.; 1 × 100 ml.). The ethereal extracts are combined, dried (Na$_2$SO$_4$), filtered and the filtrate is treated with an excess of ethereal oxalic acid solution to give 2-(N-acetyl-2-ethoxyanilino)-4-methylmorpholine hydrogen oxalate, m.p. 186-°187° C. on recrystallisation from ethanol.

The 2-(N-acetyl-2-ethoxyanilino)methyl-4-n-propylmorpholine hydrogen oxalate used as starting material may be obtained by repeating the process described in the second part of Example 9 using 2-(2-ethoxyanilino)methyl-4-n-propylmorpholine toulene-p-sulphonate in place of 4-benzyl-2-(2-ethoxyanilino)methylmorpholine. There is thus obtained 2-(N-acetyl-2-ethoxyanilino)methyl-4-n-propylmorpholine hydrogen oxalate, m.p. 161°–163° C. on recrystallisation from methanol/ether.

Some of the 4-benzyl-N-acetylanilinomethylmorpholines used as starting materials may be prepared by repeating the process described in the second part of Example 9, using the appropriate 4-benzylanilinomethylmorpholine in place of 4-benzyl-2-(2-ethoxyanilino)methylmorpholine. The following compounds are thus obtained:

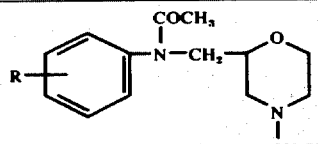

| R | Salt | m.p. (°C.) | Recrystallisation Solvent |
|---|---|---|---|
| H | oxalate | 105–107 | methanol/ether |
| 2-Cl | oxalate | 98–100 | methanol/ether |
| 2-Me | hydrochloride | 205–207 | methanol/ether |

The 2-(N-acetyl-4-methyl-2-n-propylanilino)methyl-4-benzylmorpholine oxalate used as starting material may be prepared as follows:

To a stirred suspension of sodium hydride (60% dispersion; 0.8 g.) in dry dimethylformamide (30 ml.) is added 4-methyl-2-n-propylacetanilide (3.8 g.) under nitrogen. When the effervescence has ceased, 4-benzyl-2-toluene-p-sulphonyloxymethylmorpholine (7.0 g.) is added and the resulting solution is stirred and heated at 100°–120° C. under nitrogen for 18 hours. The mixture is cooled, poured into water and the resulting mixture extracted with ethyl acetate. The organic extract is extracted with aqueous hydrochloric acid, the acidic extract is neutralised and extracted with ethyl acetate. This ethyl acetate extract is washed with water, dried (MgSO$_4$) and distilled to give a thick oil which forms an oxalate. Recrystallisation from ethyl acetate gives 2-(N-acetyl-4-methyl-2-n-propylanilino)methyl-4-benzylmorpholine oxalate, m.p. 147°–148° C.

The preparation of some of the 4-benzyl-2-anilinomethylmorpholine used as starting material is described in Example 3. Other 4-benzyl anilinomethylmorpholines used as starting materials may be prepared by repeating the process described in the second part of Example 1 using the appropriate substituted aniline in place of 2-ethoxyaniline. The following compounds are thus prepared:

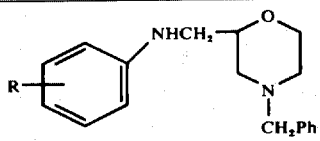

| R | Salt | m.p. (°C.) | Recrystallisation Solvent | Xylene as Solvent |
|---|---|---|---|---|
| 2-Cl | dihydrochloride | 194–196 | methanol/ether | no |
| 2-Me | toluene-p-sulphonate | 174–177 | methanol | no |

EXAMPLE 11

Crude 2-(N-acetyl-2-n-propylanilino)methyl-4-phenoxycarbonylmorpholine (3.2 g.) is heated under reflux in 50% sulphuric acid for 18 hours. The reaction mixture is cooled, diluted with water (200 ml.), basified with sodium hydroxide solution and extracted with ether (2 × 100 ml.). The extract is dried (Na$_2$SO$_4$), filtered and the filtrate is treated with an ethereal solution of oxalic acid to give 2-(2-n-propylanilino)methylmorpholine oxalate, m.p. 121°–124° C. (decomp.) on recrystallisation from ethanol/ethyl acetate.

The 2-(N-acetyl-2-n-propylanilino)methyl-4-phenoxycarbonylmorpholine used as starting material may be obtained as follows:

Sodium hydride (1.1 g. of 60% suspension in oil) is suspended in dry dimethylformamide (25 ml.) and a solution of 2-n-propylacetanilide (4.4 g.) in dry dimethylformamide is added with stirring at 20° C. during 15 minutes. The mixture is stirred for a further 30 minutes, 4-benzyl-2-toluene-p-sulphonyloxymethylmorpholine (9 g.) is then added and the temperature is raised to 95°–100° C. for 20 hours. The reaction mixture is cooled, diluted with water (300 ml.), extracted with ether (2 × 100 ml.) and the ethereal extract is dried (MgSO$_4$), filtered and the filtrate is treated with an ethereal solution of hydrochloric acid. The ether is decanted from the gummy product which is crystallised from a mixture of ethanol and ether to give 2-(N-acetyl-2-n-propylanilino)methyl-4-benzylmorpholine hydrochloride, m.p. 198°–200° C.

2-(N-Acetyl-2-n-propylanilino)methyl-4-benzylmorpholine (2.2 g.) (prepared by basification of the hydrochloride described above) is azeotroped in toluene (30 ml.) until a clear dry solution is obtained. The solution is cooled and phenylchloroformate (1.2 g.) is added and the mixture is heated under reflux for 18 hours when the toluene is removed under reduced pressure. Crude 2-(N-acetyl-2-n-propylanilino)methyl-4-phenoxycarbonylmorpholine is obtained as an orange coloured oil.

EXAMPLE 12

To a solution of 2-[3(2ethoxyanilino)-2-hydroxy]-propylaminoethyl hydrogen sulphate (6.6 g.) in methanol (20 ml.) and water (10 ml.) is added a solution of sodium hydroxide (8 g.) in water (20 ml.) and the mixture is stirred and heated at 90° C. for 18 hours. The mixture is cooled, water added, and the mixture extracted with ethyl acetate (3 × 50 ml.). The combined extracts are washed with acetic acid (10%; 3 × 50 ml.) and the combined extracts basified with sodium hydroxide and extracted with ethyl acetate. The combined ethyl acetate extracts are dried (MgSO$_4$) and evaporated and the residue is converted to its oxalate salt to give 2-(2-ethoxyanilino)methylmorpholine oxalate monohydrate, m.p. 161°–163° C. on recrystallisation from acetone/methanol.

The solution of 2-[3-(2-ethoxyanilino)-2-hydroxy]-propylaminoethyl hydrogen sulphate used as starting material may be obtained as follows:

A solution of 1-chloro-3-(2-ethoxyanilino)propan-2-ol, prepared by the method described in *Chem. Ber.*, 1904, 37, 3034 from 2-ethoxyaniline and epichlorhydrin, in methanol (20 ml.) is added to a stirred mixture of 2-aminoethyl hydrogen sulphate (14.1 g.) and sodium hydroxide (4.0 g.) in water (10 ml.), and this mixture is stirred at ambient temperature for 2 hours.

Alternatively, the solution of 2-[3-(2-ethoxyanilino)-2-hydroxy]propylaminoethyl hydrogen sulphate may be obtained as follows:

A mixture of 2-ethoxyaniline (54.8 g.), methanol (300 ml.) and epichlorhydrin (18.6 g.) is stirred at 25° C. for 24 hours. The methanol and unreacted 2-ethoxyaniline are removed by vacuum distillation and the residue is dissolved in methanol (300 ml.) and sodium hydroxide (8.0 g.) added. The mixture is stirred at 25° C. for 3 hours, filtered and the filtrate evaporated under reduced pressure to give N-glycidyl-2-ethoxyaniline which is then dissolved in methanol (69 ml.). This solution is added to a stirred suspension of 2-aminoethyl hydrogen sulphate (97.0 g.) in a mixture of methanol (69 ml.), water (16.5 ml.) and sodium hydroxide solution (17 N; 35.0 ml.). The mixture is stirred at 25° C. for 16 hours.

EXAMPLE 13

A solution of (2S)-4-benzyl-2-(2-ethoxyanilino)methylmorpholine dihydrochloride (5 g.) in a mixture of ethanol (50 ml.) and water (5 ml.) is shaken in an atmosphere of hydrogen with palladium on carbon catalyst (0.5 g. 5%) until no more hydrogen is absorbed. The catalyst is removed by filtration and the filtrate is evaporated under reduced pressure when (2S)-2-(2-ethoxyanilino)methylmorpholine dihydrochloride (3.7 g.) is obtained as a hygroscopic solid. The dihydrochloride is dissolved in water (100 ml.), the solution is basified with sodium hydroxide solution and extracted with ether (2 × 100 ml.). The ethereal extract is dried ($Na_2SO_4$), filtered and the filtrate is then carefully titrated with an ethereal solution of hydrogen chloride to given (2S)-2-(2-ethoxyanilino)methylmorpholine hydrochloride, m.p. 150°–159° C. on recrystallisation from ethanol $[\alpha]_D^{28}$ − 2.2° (c,4 in methanol).

The (2S)-4-benzyl-2-(2-ethoxyanilino)methylmorpholine dihydrochloride used as starting material may be obtained as follows:

To a solution of 4-benzyl-2-(toluene-p-sulphonyloxy)methylmorpholine (18.1 g.) in methanol (100 ml.) is added a solution of (+)-toluene-p-sulphonylglutamic acid (16.0 g.) in methanol (50 ml.) and the mixture is allowed to crystallise during twelve hours. The mixture is filtered and the residue (18.3 g.) is recrystallised from methanol (150 ml.) to obtain the (+)-toluene-p-sulphonylglutamic acid salt of (2S)-4-benzyl-2-(toluene-p-sulphonyloxy)methylmorpholine (14.0 g.), m.p. 184° C. This salt is stirred with a mixture of 2N sodium hydroxide and ether. The ether layer is separated, dried and the ether is distilled to leave optically pure (2S)-4-benzyl-2-(toluene-p-sulphonyloxy)methylmorpholine as an oil from which is prepared the hydrochloride, m.p. 150° C., $[\alpha]_D^{25}$ + 19.4° (c,5 in methanol).

A mixture of (2S)-4-benzyl-2-(toluene-p-sulphonyloxy)methylmorpholine (5.5 g.) and o-phenetidine (10 g.) is heated at 95°–100° C., in an atmosphere of nitrogen, for 18 hours. The sticky resin thus obtained is cooled and washed with ether (250 ml.) and then shaken with ether (250 ml.) and dilute sodium hydroxide solution (250 ml.;8%). The ethereal solution is washed with water (2 × 100 ml.), dried ($Na_2SO_4$), filtered and the filtrate is then treated with an ethereal solution of hydrochloride acid. The precipitated dihydrochloride is crystallised from a mixture of methanol-/ethyl acetate to give (2S)-4-benzyl-2-(2-ethoxyanilino)methylmorpholine dihydrochloride, m.p. 232°–234° C. (decomposition) $[\alpha]_D^{25}$ + 34.1° (c,4 in methanol).

EXAMPLE 14

The process described in the first part of Example 13 is repeated except that (2R)-4-benzyl-2-(2-ethoxyanilino)methylmorpholine dihydrochloride is used as starting material in place of the corresponding (2S) isomer. There is thus obtained (2R)-2-(2-ethoxyanilino)methylmorpholine hydrochloride, m.p. 158°–159° C. $[\alpha]_D^{27}$ + 1.8° (c,4 in methanol).

The (2R)-4-benzyl-2-(2-ethoxyanilino)methylmorpholine dihydrochloride used as starting material may be obtained as follows:

The methanol mother liquor obtained after isolation of the (S) isomer of the (+)-toluene-p-sulphonyl glutamic acid salt of 4-benzyl-2-(toulene-p-sulphonyloxy)-methylmorpholine described in Example 13 is concentrated to a small volume and to this mixture 2N sodium hydroxide is added to liberate the (R)-rich base. The latter is extracted into ether, the solution is washed, dried and evaporated to an oil. The oil is dissolved in ethanol (30 ml.) and to this solution is added a solution of (+)-0,0-dibenzoyltartaric acid (10.5 g.) in ethanol (20 ml.) and the mixture is allowed to crystallise during twelve hours. The mixture is filtered and the residue is recrystallised from ethanol (100 ml.) to obtain the (+)-0,0-dibenzoyltartaric acid salt of (2R)-4-benzyl-2-(toluene-p-sulphonyloxy)methylmorpholine, m.p. 160° C. From this is obtained in the usual manner, by treatment with sodium hydroxide, optically pure (2R)-4-benzyl-2-)toluene-p-sulphonyloxy)methylmorpholine as an oil, hydrochloride m.p. 150° C. $[\alpha]_D^{25}$ −19.4° (c,5 in methanol).

The process described in the third part of Example 13 is repeated using (2R)-4-benzyl-2-(toluene-p-sulphonyloxy)methylmorpholine hydrochloride in place of the corresponding (2S) isomer. There is thus obtained (2R)-4-benzyl-2-(2-ethoxyanilino)methylmorholine dihydrochloride, m.p. 232°–234° C. (decomposition), $[\alpha]_D^{29}$ − 38.7° (c, 4 in methanol).

EXAMPLE 15

The process described in the first part of Example 13 is repeated except that (2S)-4-benzyl-2-(2-n-propoxyanilino)methylmorholine dihydrochloride is used as starting material in place of the corresponding 2-ethoxy analogue. There is thus obtained (2S)-2-(2-n-propoxyanilino)methylmorpholine hydrochloride, m.p. 154°–156° C. on recrystallisation from ethanol/ether, $[\alpha]_D^{25}$−0.6° (c,2.5 in methanol).

The (2S)-4-benzyl-2-(2-n-propoxyanilino)methylmorpholine dihydrochloride used as starting material may be obtained by repeating the process described in the third part of Example 11, using 2-n-propoxyaniline in place of o-phenetidine and carrying out the reaction in refluxing xylene for 18 hours. There is thus obtained (2S)-4-benzyl-2-(2-n-propoxyanilino)methylmorpholine dihydrochloride, m.p. 192°–195° C. on recrystallisation from ethanol/ethyl acetate, $[\alpha_D^{27}$ + 37.4° (c, 2.5 in methanol).

EXAMPLE 16

The process described in the first part of Example 14 is repeated except that (2R)-4-benzyl-2-(2-n-propoxyanilino)methylmorpholine dihydrochloride is used as starting material in place of the corresponding 2-ethoxy analogue. There is thus obtained (2R)-2-(2-n-propoxyanilino)methylmorpholine hydrochloride, m.p. 152°–154° C., $[\alpha]_D^{25}$− 0.54° (c, 2.4 in methanol).

The (2R)-4-benzyl-2-(2-n-propoxyanilino)methylmorpholine used as starting material may be obtained by repeating the process described in the third part of Example 14, using 2-n-propoxyaniline in place of o-phenetidine and carrying out the reaction in refluxing xylene for 18 hours. There is thus obtained (2R)-4-benzyl-2-(2-n-propoxyanilino)methylmorpholine, m.p.

192°–195° C. on recrystallisation from ethanol/ethyl acetate, $[\alpha]_D^{26}$ – 37.5° (c, 2.5 in methanol).

What we claim is:

1. A pharmaceutical composition for treating or preventing depression which comprises as active ingredient an effective amount of morpholine selected from a compound of the formula:

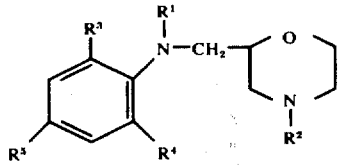

wherein $R^1$ is hydrogen or hydrocarbon aryloxycarbonyl of up to 11 carbon atoms; $R^2$ is hydrogen or alkyl of 1 to 6 carbon atoms; and $R^3$, $R^4$ and $R^5$, which may be the same or different, are hydrogen, halogen, alkyl or alkylthio of 1 to 6 carbon atoms, halogenoalkyl of 1 to 3 carbon atoms, alkoxy of 1 to 10 carbon atoms, alkenyloxy or alkoxycarbonyl of up to 6 carbon atoms, hydrocarbon aroyl of up to 11 carbon atoms, hydrocarbon aryl, hydrocarbon aryloxy or hydrocarbon arylthio of up to 10 carbon atoms; and a non-toxic pharmaceutically-acceptable acid-addition salt thereof, in association with a major amount of a non-toxic, pharmaceutically-acceptable diluent or carrier.

2. A method of relieving or preventing depression in warm-blooded animals including man which comprises administering to said warm-blooded animal an antidepressantly effective amount of a compound selected from a compound of the formula:

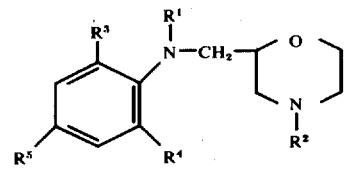

wherein $R^1$ is hydrogen or hydrocarbon aryloxycarbonyl of up to 11 carbon atoms; $R^2$ is hydrogen or alkyl of 1 to 6 carbon atoms; and $R^3$, $R^4$ and $R^5$, which may be the same or different, are hydrogen, halogen, alkyl or alkylthio of 1 to 6 carbon atoms, halogenoalkyl of 1 to 3 carbon atoms, alkoxy of 1 to 10 carbon atoms, alkenyloxy or alkoxycarbonyl of up to 6 carbon atoms, hydrocarbon aroyl of up to 11 carbon atoms, hydrocarbon aryl, hydrocarbon aryloxy or hydrocarbon arylthio of up to 10 carbon atoms; and a non-toxic, pharmaceutically-acceptable acid-addition salt thereof.

3. A method according to claim 2 wherein the morpholine is one where $R^1$ is hydrogen or phenoxycarbonyl; $R^2$ is hydrogen or methyl, ethyl, n-propyl or i-propyl; and $R^3$, $R^4$ and $R^5$ are hydrogen, chlorine, fluorine, methyl, ethyl, n-propyl, i-propyl, methylthio, trifluoromethyl, methoxy, ethoxy, n-propoxy, i-propoxy, n-butoxy, s-butoxy, n-pentyloxy, n-hexyloxy, n-octyloxy, allyloxy, methoxycarbonyl, benzoyl, phenyl, phenoxy or phenylthio.

4. A method according to claim 2 wherein the morpholine is selected from the group consisting of 2-(2-ethoxyanilino)methylmorpholine, 2-(2-n-propoxyanilino)methylmorpholine, 2-(2-i-propoxyanilino)-methylmorpholine, 2-(2-s-butoxyanilino)methylmorpholine and 2-(2-phenoxyanilino)methylmorpholine.

* * * * *